United States Patent [19]

Lee

[11] Patent Number: 5,629,008
[45] Date of Patent: May 13, 1997

[54] METHOD AND DEVICE FOR LONG-TERM DELIVERY OF DRUGS

[75] Inventor: Clarence C. Lee, Lilburn, Ga.

[73] Assignee: C.R. Bard, Inc., Murray Hill, N.J.

[21] Appl. No.: 255,343

[22] Filed: Jun. 7, 1994

Related U.S. Application Data

[63] Continuation-in-part of Ser. No. 892,204, Jun. 2, 1992, abandoned.

[51] Int. Cl.⁶ .................................. A61F 2/02; A61K 9/22
[52] U.S. Cl. .......................... 424/426; 424/424; 604/892.1
[58] Field of Search .................................. 424/423, 424, 424/426; 604/892.1

[56] References Cited

U.S. PATENT DOCUMENTS

| Re. 32,969 | 6/1989 | Trager et al. | 424/78.04 |
|---|---|---|---|
| 3,710,795 | 1/1973 | Higushi et al. | 424/423 |
| 4,179,846 | 12/1979 | Bucalo | 604/51 |
| 4,595,583 | 6/1986 | Eckenhoff et al. | 424/438 |
| 4,627,851 | 12/1986 | Wong et al. | 424/473 |
| 4,693,895 | 9/1987 | Wong et al. | 424/473 |
| 4,723,950 | 2/1988 | Lee | 604/322 |
| 4,725,442 | 2/1988 | Haynes | 424/490 |
| 4,775,659 | 10/1988 | Thakkas et al. | 514/2 |
| 4,792,448 | 12/1988 | Ranade | 424/467 |
| 4,803,075 | 2/1989 | Wallace et al. | 424/423 |
| 4,822,368 | 4/1989 | Collier | 623/22 |
| 4,828,828 | 5/1989 | Trager et al. | 424/424 |
| 4,871,542 | 10/1989 | Vilhardt | 424/426 |
| 4,913,903 | 4/1990 | Sudmann et al. | 424/426 |
| 5,059,423 | 10/1991 | Magruder et al. | 604/322 |

FOREIGN PATENT DOCUMENTS

| 0164241 | 12/1985 | European Pat. Off. . |
|---|---|---|
| 0572932 | 12/1993 | European Pat. Off. . |
| 0572932A2 | 12/1993 | European Pat. Off. . |

OTHER PUBLICATIONS

*Stedman's Medical Dictionary*, 24th edition, Williams & Wilkins, Baltimore, p. 171 (definition for "biodegradable").

*Primary Examiner*—Carlos A. Azpuru
*Attorney, Agent, or Firm*—Jones & Askew

[57] ABSTRACT

The present invention is an implantable device that is capable of delivering a therapeutic agent to a tissue or organ over a long period of time. The implantable device is especially suited for treating tissues and organs that are comprised of smooth muscle. The implantable device can deliver either a single therapeutic agent or a plurality of therapeutic agents to the tissue or organ at zero order kinetics.

24 Claims, 1 Drawing Sheet

METHOD AND DEVICE FOR LONG-TERM DELIVERY OF DRUGS

CROSS-REFERENCE TO RELATED APPLICATIONS

This application is a continuation-in-part of U.S. application Ser. No. 07/892,204, filed Jun. 2, 1992, now abandoned.

FIELD OF THE INVENTION

The present invention relates to a method and device for delivering therapeutic agents to a tissue or organ. More particularly, the present invention relates to a method and device for the long-term delivery of a drug or a plurality of drugs directly to a target smooth muscle tissue or organ.

BACKGROUND OF THE INVENTION

Many organs and glands in the body contain smooth muscles that differ from skeletal muscle in smooth muscles are not under voluntary control and do not have a striated or banded appearance under the light microscope. These smooth muscles lack striations because their contractile filaments are not organized in regular arrays of aligned sarcomeres. Smooth muscles are specialized for long, slow contractions. Rather than taking instructions from motor neurons with cell bodies in the central nervous system, they are controlled by nerve fibers of the autonomic nervous system and by circulating hormones.

Smooth muscles perform a wide variety of functions. They control the diameter of arterioles and thus help regulate pressure. They form muscular sphincters at branches of the vascular tree and thus determine the distribution of blood to different capillary beds. Gastrointestinal sphincters control passage of intestinal contents from one section of the gut to the next. Smooth muscles regulate the size and internal pressure in hollow organs such as the urinary bladder and the uterus. Smooth muscles vary greatly in electrical activity, degree of automaticity, innervation, response to the circulating hormones and drugs, and extent of cell-to-cell coupling. (For a review of smooth muscles, see Stephens, N. L., *Smooth Muscle Contraction*, New York, M. Dekker, (1984)).

In unitary smooth muscle, contraction is synchronized so that the muscle acts as a unit, all fibers either contracting or resting. Unitary muscles are spontaneously active, display electrical pacemaker activity, and respond to stretch with increased activity. The innervation density is low, and the cells are tightly coupled electrically through gap junctions so that activity, once initiated, spreads promptly from cell to cell. The multicellular muscle acts as a single unit. Unitary smooth muscle thus resembles cardiac muscle more closely than striated muscle. Examples are the gut and uterus, organs that generate and propagate their own slow, rhythmic movements.

Time release delivery of drugs to a smooth muscle tissue or an organ is desired where there is a requirement for long-term administration of the drug to the tissue or organ. In addition, it is often advantageous to be able to deliver a drug directly to the site which needs to be treated and thereby avoid systemic administration of the drug. This is especially true where the drug may be harmful to certain other tissues or organs if administered systemically. Localized delivery would allow one to deliver high concentrations of the desired drug to a specific region of the body and yet not harm other tissues and organs.

Currently available therapies designed to externally regulate the contraction of internal organs are limited to electro-stimulation of specific diseased organ and/or systemic administration of musculotropic agents and/or neurochemicals. The implantation of a permanent electro-stimulator exposes patients to potential risks associated with major surgery and general anesthesia. The malfunctioning or infection of the electro-stimulation implant can further complicate or reverse the prognosis of these patients.

It is well-known that systemic administration of neurochemicals and/or musculotropic agents often adversely affects other non-diseased organs and tissues. The possible side effects can include dry mouth, blurred vision, mydriasis, tachycardia, drowsiness and constipation. In general, patients with glaucoma or a heart condition are excluded from systemic administration of these types of agents. Thus, the localized controlled administration of neurochemicals and/or musculotropic agents would optimize their effects on the targeted organs without significantly affecting other organs or nerve systems.

Several patents describe short-term delivery compositions and devices. U.S. Pat. No. 4,913,903 discloses a biodegradable polymer which can be admixed with a therapeutic agent and implanted into the body allowing short-term release of a therapeutic agent. The polymer is based upon two polyorthoesters and forms a solid polymer. The polymer disclosed in the '903 patent is designed to release chemotherapeutic agents over a relatively short period of time such as the convalescent period after surgery. The biodegradable polymer disclosed in the '903 patent would not be useful in the situation where long-term administration, i.e., one to two years, is necessary.

U.S. Pat. No. 4,871,542 discloses a method and apparatus for delivering therapeutic agents to the interior of the bladder and the urinary tract. The device disclosed in the '542 patent is a porous, minicellular polymeric container which acts as a reservoir for a therapeutic agent. The size of the minicellular pores regulates the rate of diffusion of the therapeutic agent. The device described in the '542 patent would not be suitable for implantation into a tissue for the long-term administration of a therapeutic agent.

U.S. Pat. No. 4,775,659 discloses an injectable, time-release formulation comprising a therapeutic agent, an oil and a suitable glyceride release modifying agent. The composition is injected intramuscularly, and the therapeutic agent is released over a period of days. The formulation described in the '659 patent would not be appropriate for the long-term delivery of a therapeutic agent to a tissue or organ.

U.S. Pat. No. 4,792,448 discloses a device wherein the matrix material is made of an inert material which either dissolves into the surrounding fluid or is insoluble and retains its original shape. To achieve long-term delivery of a therapeutic agent, the device disclosed in the '448 patent would be too large to be used as an injectable implant.

Finally, U.S. Pat. No. 4,725,442 discloses injectable microdroplets containing water-insoluble drugs. The preferred use of the microdroplets is the localized, time-release delivery of anesthetics. Again, the release of the water-insoluble drug from the microdroplets is disclosed as being useful only for a period of days. The microdroplets disclosed in the '442 patent would not be suitable for release of a biologically active agent over a period of months to years.

What is needed is an injectable device which can be implanted directly into the target tissue and which is capable of releasing a biologically active agent over a period of time. Such an injectable device would be particularly effective in treating patients with bladder instability etiology.

SUMMARY OF THE INVENTION

The present invention is a device and method for the long-term local delivery of a therapeutic agent to a tissue or organ. The present invention includes a device comprising a container with a biodegradable matrix therein. The biodegradable matrix is admixed with a therapeutic agent. The container can be implanted into a tissue and will deliver a desired therapeutic agent over a period of months to years.

More particularly, the present invention is an implant device for the long-term delivery of a therapeutic agent to a tissue or organ, comprising a container for implantation within the tissue or organ, a therapeutic agent contained within the container; and means associated with at least one of the container and the therapeutic agent for controlling the rate of release of the therapeutic agent from the container into the tissue or organ such that the therapeutic agent is released at a rate of between approximately 0.1 µg to approximately 12 mg/day over a period of at least one month.

In a preferred embodiment, the container is a cylinder with at least one opening to the tissue in which the cylinder is implanted. The cylinder can be manufactured from silicone, stainless steel, titanium or other types of medical/surgical grade plastics or metals. Plastics that can be used in constructing the present invention include, but are not limited to, polyethylene, polypropylene and parylene. The cylinder walls are impermeable to enzymes or other macromolecules and optionally are impermeable to water. Macromolecules are defined herein as molecules with a molecular weight greater than approximately 10,000 Daltons.

In one aspect, the present invention is particularly suited for the administration of musculotropic or neurochemicals to smooth muscle tissues. Tissues and organs that can benefit from the present invention include, but are not limited to, stomach, intestines, heart, uterine, bladder, ureter, urethra, sphincter muscles, and the esophagus.

In one embodiment, the present invention is designed to reduce or eliminate incontinence frequency with pure detrusor instability or with a combination of stress urinary incontinence and detrusor instability without any upper motor neuron lesion. The device can effectively deliver therapeutic agents for at least one month and is reimplantable. The implant can be performed in the doctor's office or on an outpatient basis.

Accordingly, it is an object of the present invention to provide a device and method for localized long-term administration of a therapeutic agent to a particular tissue or organ.

It is another object of the present invention to provide a device and method for the long-term delivery of a musculotropic or neurochemical to smooth muscle tissue.

It is another object of the present invention to provide a device and method for treatment of patients who are incontinent with bladder instability etiology.

It is a further object of the present invention to provide long-term delivery of a therapeutic agent immobilized in a biodegradable matrix within a container.

It is a further object of the present invention to provide a device and method for the treatment of smooth muscle.

It is also a further object of the present invention to provide an implantable device.

These and other objects, features and advantages will become apparent after a review of the following detailed description of the disclosed embodiments and the appended claims.

DETAILED DESCRIPTION

Figure 1:
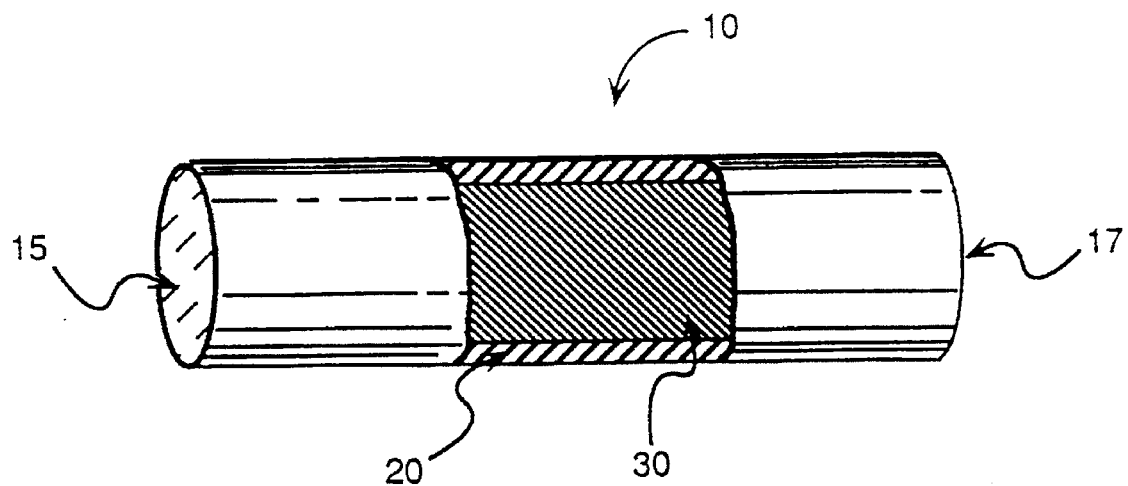
FIG. 1 is a side view of an apparatus useful for the long-term delivery of a therapeutic agent to a tissue or organ.

The present invention comprises an apparatus and method for the localized, long-term treatment of a tissue or organ. The present invention is especially suited for the long-term treatment of smooth muscle tissues and organs. The present invention comprises an implant device for the long term delivery of a therapeutic agent to a tissue or organ, comprising a container for implantation within the tissue or organ, and a therapeutic agent immobilized in a biodegradable matrix and contained within the container such that the therapeutic agent is released at a rate of at least approximately 0.1 µg/day over a period of at least approximately one month.

The present invention can be used for localized time release delivery of drugs to a specific tissue or organ that can be classified as mechanically dynamic organs. Examples of mechanically dynamic organs include, but are not limited to, the stomach, intestines, heart, bladder, ureter, urethra, various sphincter muscles, and the esophagus. The functions of these organs are maintained by their normal and timely mechanical contractions. Should the mechanical properties be lost, the intended functions of these organs are partially or completely lost.

The mechanical contractions are dependent on the states of the constituent smooth muscle and the nerve systems involved. Factors which affect the contractions of these organs include anxiety, biochemical or hormonal imbalance, smooth muscle disease or dysfunction, and lesions of central or peripheral nerves. A specific example can be seen when stress can ultimately effect one's stomach contractions thereby causing ulcers in some individuals. Uterine cramps in women can be caused by anxiety, biochemical and/or hormonal imbalances. Peripheral neural lesions can cause urge incontinence.

Smooth muscle contractions can be modulated by a long-term drug delivery regimen according to the present invention. Insertion of the long-term delivery device according to the present invention, with the appropriate pharmaceutical agent, into uterine or gastric muscle can inhibit contraction of those muscles. Long-term delivery devices can be inserted to control the contractions of smooth muscle found in vascular vessels and thus regulate the overall blood pressure of the body.

The present invention, in one embodiment, is an apparatus comprising a container containing a therapeutic agent that has been physically trapped, or covalently or ionically immobilized, in a biodegradable matrix. The therapeutic agents can be physically trapped in the matrix by mixing, ionic bonding on the matrix and/or covalent bonding via irradiation or through the use of cross-linkers including, but not limited to, glutaraldehyde, polyethylene glycol epoxide or ethylene oxide. In a preferred embodiment, the biodegradable matrix is in the form of a cylinder. The sides of the cylinder preferably include an impermeable coating. One or both ends of the cylinder can be open to the tissue, or the cylinder ends may be covered with a water-permeable membrane.

A critical element of the device of the present invention is the biodegradable matrix. A biodegradable matrix, as used herein, is a matrix made of materials, usually polymers, which are degradable by enzymatic or acid/base hydrolysis. Once inserted into the body, the matrix is acted upon by enzymes and body fluids. Biodegradation, as used herein, is a process which is different from the process of dissolution. Dissolution occurs as a function of the solute properties of the material. With a dissolving matrix, the therapeutic agent is released as the matrix dissolves. Thus, the length of time the device will release the therapeutic agent is a function of the amount of therapeutic agent within the matrix. For long-term release, the device would have to be quite large to provide a continuous supply of the therapeutic agent. A matrix which is biodegradable only releases the therapeutic agent as the matrix is acted upon by body fluids or enzymes.

The biodegradability of the matrix controls the rate of release of the therapeutic agent. The therapeutic agent does not diffuse out of the matrix, but is only released as the matrix is biodegraded. Because the matrix is biodegradable, there is no residue of the matrix remaining when the entire dose of the therapeutic agent has been delivered. Because there is no residual matrix remaining, there is no need to remove the device.

Figure 2:
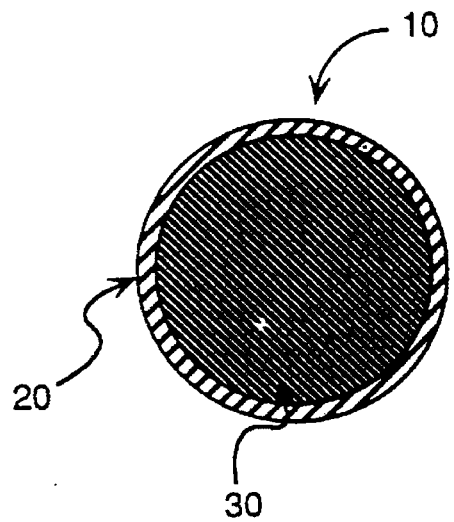
FIG. 2 is a cross-sectional view of the apparatus shown in FIG. 1.

As shown in FIG. 1, one embodiment of the present invention comprises a cylinder 10 including a wall 20 that is preferably non-permeable to macromolecules such as proteins and cells. The cylinder wall 20 can be made of medical-grade silicone, stainless steel, titanium, gold, or plastics. The cylinder 10 is filled with a biodegradable matrix 30 with a therapeutic admixed therein. The ends 15, 17 of the cylinder 10 are preferably open to the tissue. Alternatively, the ends 15, 17 of the cylinder can be covered with a membrane that is permeable to water, macromolecules and optionally to cells. In another embodiment of the present invention, one end 15 of the cylinder 10 can be sealed with a material that is impermeable to enzymes and cells and the other end of the cylinder 10 can be open to tissue. FIG. 2 is a cross-sectional view of cylinder 10 showing the cylinder wall 20 and the biodegradable matrix 30 therein.

In a preferred embodiment of the present invention, the device is preferably between 0.1 cm and 3.0 cm in length and preferably between 0.1 cm and 3.0 cm in diameter. It is to be understood that while a cylinder is the preferred shape of the device that is contemplated as the present invention, the device can be any other shape including, but not limited to, a disc, or a ring.

The long-term delivery device can also have a diameter which ranges in size from 20 microns to 3,000 microns and length which can range in size from 20 microns to 3,000 microns. One micron is defined as $1 \times 10^{-6}$ meters. In a more preferred embodiment of the present invention, the device is between 20 to 200 microns in length and between 20 to 200 microns in diameter.

It is to be understood that while a cylinder is the preferred shape of the device that is contemplated as the present invention, the device can be any other shape including, but not limited to, a disc, a rectangle or a ring. A preferred embodiment of a disc would have the dimensions of 120 microns in diameter and 120 microns in thickness. A preferred embodiment of a rectangle would be 1.2 mm long, 1.0 mm wide and 1.0 mm thick. A preferred embodiment of a ring would have the dimensions of 1.2 mm outer diameter and 200 microns inner diameter.

The biodegradable matrix that is placed inside the cylinder can be a matrix chosen from biocompatible materials such as liposomes, polylactides (polylactic acid), polyglycolide (polymer of glycolic acid), polylactide co-glycolide (co-polymers of lactic acid and glycolic acid) polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

The therapeutic agents can be any compound that is biologically active and requires long term administration to a tissue or organ for maximum efficacy. Therapeutic agents that can be used in accordance with the present invention include, but are not limited to, antimuscarinic agents, anticholinergic agents, antispasmodic agents, calcium antagonist agents, potassium channel openers, musculotropic relaxants, antineoplastic agents, polysynaptic inhibitors, and beta-adrenergic stimulators. Examples of anticholinergic agents are propantheline bromide, imipramine, mepenzolate bromide, isopropamide iodide, clidinium bromide, anisotropine methyl bromide, scopolamine hydrochloride, and their derivatives. Examples of antimuscarinic agents include, but are not limited to, hyoscyamine sulfate, atropine, methantheline bromide, emepronium bromide, anisotropine methyl bromide, and their derivatives. Examples of polysynaptic inhibitors are baclofen and its derivatives. Examples of β-adrenergic stimulators are terbutaline and its derivatives. Examples of calcium antagonists are terodiline and its derivatives. Examples of musculotropic relaxants include, but are not limited to, dicyclomine hydrochloride, flavoxate hydrochloride, papaverine hydrochloride, oxybutynin chloride, and their derivatives. Examples of an antineoplastic agents include, but are not limited to, carmustine levamisole hydrochloride, flutamide, (w-methyl-N-[4-nitro-3-(trifluoromethyl) phenyl]), adriamycin, doxorubicin hydrochloride, idamycin, fluorouracil, cytoxan, mutamycin, mustargen and leucovorin calcium. Examples of antispasmodic agents are hexadiphane, magnesium gluconate, oktaverine, alibendon, butamiverine, hexahydroadiphene, 2-piperidinoethyl 3-methylflavone-8-carboxylate, 4-methylumbelliferone 0,0-diethyl phosphorothiate. Examples of potassium channel openers are pinacidil and N-[-2-Nitrooxy)ethyl]-3-pyridinecarboxamide.

It is important that the kinetics of the therapeutic agent release be zero order kinetics or near zero order kinetics. The rate of release of the therapeutic agent will vary depending upon the target tissue or organ and on the therapeutic agent or agents being delivered. The rate of release of the therapeutic agent can be controlled by the choice of active ingredients with different solubilities and biodegradable matrix, how the therapeutic agent is physically trapped or chemically immobilized in the biodegradable matrix, by varying the area of the biodegradable matrix exposed to the tissue by adjusting the area of the opening in the container, and/or adjusting the permeability of the walls and/or opening to the therapeutic agent.

Musculotropic relaxants are direct acting smooth muscle depressants and act directly on the smooth muscle at sites distal to the cholinergic receptors. β-adrenergic stimulators stimulate the relaxation mediating beta receptors in smooth muscle. Calcium antagonists relax many types of smooth muscle. The calcium antagonist would decrease or inhibit the influx of calcium ion into smooth muscles and/or activate the calcium pump to pump calcium ions out of smooth muscle into extracellular fluids. Because all types of smooth muscle have poorly developed sarcoplasmic reticuli for storing calcium ions, the calcium source for smooth muscle relaxation is always the extracellular fluid. Antimuscarinic inhibitors prevent the effects of parasympathetic stimulation at the neuroeffector junction. These antimuscarinic agents result in parasympathetic stimulation at the neuroeffector junction. Polysynaptic inhibitors relax smooth muscle by acting on nerve cells in the neural conduction pathways formed by a chain of many synaptically connected nerve cells.

The invention is further illustrated by the following examples, which are not to be construed in any way as imposing limitations upon the scope thereof. On the contrary, it is to be clearly understood that resort may be had to various other embodiments, modifications and equivalents thereof which, after reading the description herein, may suggest themselves to those skilled in the art without departing from the spirit of the present invention and/or the scope of the appended claims.

EXAMPLE I

Polylactide and oxybutynin chloride powder (5:1 by weight) are blended by mechanical stirring and extruded at approximately 140° C. to form a long cable (3-mm in diameter). The cable is cut into 1 inch pellets. One end of these pellets is blocked with a biocompatible silicone (RTV) adhesive. With the blocked end facing downwards, the pellets are placed on a turntable inside a vacuum chamber. After desirable vacuum is reached (approximately $10^{-10}$ mBar), the DC current is turned on and the voltage is increased until sparks occur at the 24K gold wire electrode. The gold wire electrode must be positioned above the top of the pellets and at an angle to them. The gold is spattered on the surface of the rotating rods until a minimum of 100 Å thick gold coating is achieved. The adhesive top is then removed by either peeling or mechanical abrasion.

EXAMPLE II

Polyglycolide and hyoscyamine sulfate powder (20:1 by weight) are blended by stirring and extruded at approximately 160° C. to form a 5-inch rod (1 mm in diameter). The rod is rotated around its axis while it is coated with pure platinum by vacuum deposit to reach a 10 micron thickness. Then the rod is cut into half-inch segments. An 18-gauge, 3 ½ inch needle with a styler is used to deliver the pellet directly into the bladder neck tissue of a female patient. The needle with a stylet in place is inserted perineally and parallel to the inserted cystoscope. With the aid of the scope, the tip of the needle is located while it is advanced toward the bladder neck. When the tip is approximately one inch from the bladder neck, the stylet is removed while holding the needle immobile. Approximately 0.3 cc of USP grade glycerol is injected into the needle lumen. The ½ inch rod is then inserted into the lumen of the needle, then the rod is pushed into the bladder neck tissue using the stylet. The glycerol functions as a lubricant and protective layer during the insertion of the rod into the bladder neck tissue.

EXAMPLE III

Polyanhydride, a copolymer of bis (p-carboxyphenoxy) propane and sebacic acid at a ratio of 20:80 is mixed with Terodiline ((N-(1,1-dimethylethyl)-α-methyl-γ-phenylbenzenepropanamine). The mixture is then molded into 10 mm by 3 mm pellets. The pellets are coated with gold as described in Example I. One end is not blocked. A trocar-sleeve system is used to deliver the pellet to the periurethral tissue. The Terodiline is delivered from the coated pellet at a zero order kinetic rate of >1.7 µg/hour.

EXAMPLE IV

Polyanhydride copolymer is mixed with the antineoplastic agent carmustine (N,N-bis(2-chloroethyl)-N-nitrosourea) and atropine. A pellet is formed with the dimensions of 10 mm (L) by 4 mm (D). The pellets are coated with gold on the sides and on one end. One end is left open. After a cancer patient's prostatic tumor is removed, one pellet is left at the surgical site prior to suture. When the carmustine and atropine are exhausted from the pellet, a second pellet can be delivered, if necessary, through a working channel of an endoscope.

EXAMPLE V

A stainless steel cylindrical container with inner and outer dimensions of 1.5 cm (L)×1.0 cm (inside measurements)× 1.7 cm (L)×1.4 cm (outside measurements) respectively is packed with propantheline and polylactic acid (1:50) and compressed under pressure. The open end is sealed with a nitrocellulose membrane. This cylindrical device is then implanted either surgically or through an endoscope into the stomach wall of a cow suffering from chronic emetics.

EXAMPLE VI

Fibers (0.2 mm in diameter) made of polyglycolide/propantheline(80:20) and polylactide/ methscopolamine (50:50) are extruded into silicone (RTV) for coating. Then the two coated fibers are cut into 1.0 mm segments. The segments of polyglycolide/propantheline fiber and segments of polylactide/methscopolamine fiber are mixed in USP grade glycerol. The suspended material is then injected endoscopically into the stomach wall of cattle with emetics using a 14-gauge catheter needle.

EXAMPLE VII

Blend 20 g of USP-grade hyoscyamine sulfate with 10 kg of USP-grade polylactide polymer. A fiber is made by extruding the blend through an orifice of 20 microns in diameter. It is then coated with 5 micron thick silicone elastomer, and cut into 20 microns length. Approximately 150 mg of the material is packaged in a vial under vacuum and gamma-irradiated with 2.5 mRAD. The device is ready to be suspended in polyethylene glycol prior to injection into the patient's bladder wall.

EXAMPLE VIII

Four grams of USP-grade atropin sulfate is blended into 10 kg of polylactide-glycolide co-polymer. The fiber is made by extruding the blend through an orifice of 90 microns in diameter. It is coated with a 10-micron layer of gold using the vacuum sputtering method and then cut into 80 micron lengths. Approximately 150 mg of material is packaged in a vial under dry nitrogen and gamma-irradiated with 2.0 mRAD. The device is then suspended in polyethylene glycol fluid prior to injecting into the patient's bladder wall.

EXAMPLE IX

Blend 1 kg of oxybutynin chloride with 9 kg of polyglycolide. The fiber is made by extruding the blend of the active ingredient and biodegradable polymer though an orifice of 50 microns in diameter. The extruded fiber is spray-coated with aliphatic polyurethane and cut into 90 micron lengths. One hundred mg of the material is packaged in a clean vial and sealed. The device is gamma-irradiated and ready to be suspended in 1.0 ml of glycerin prior to injecting into the patient's bladder wall.

EXAMPLE X

The procedure of Example IX is followed except that the matrix is selected from Table 1 below.

TABLE 1

| | |
|---|---|
| Liposomes | Polylactide |
| Polyglycolide | Polylactide-polyglycolide copolymer |
| Polyanhydride | Poly(ortho)esters |
| Hyaluronic acid | Collagen |
| Chondroitin sulfate | Nucleic acids |
| Amino acids | Polyvinyl propylene |
| Polyvinylpyrrolidone | Silicone |
| Polymers | Specification or Size |
| Dicarboxylic acids | 8–20 Carbons |
| Fatty acids | 6–20 carbons |
| Phospholipids | lecithins |
| | phosphatidyl serine |
| | plasmologens |
| | phosphatidyl glycerol |
| | cephalins |
| | lysoglycerophosphatide |
| | cardiolipin |
| | sphingosine phosphate |
| | Derivatives and combinations |
| Polypeptides | polyalanine |
| | polyvaline |
| | polyleucine |
| | polyisoleucine |
| | polyphenylalanine |
| | Combinations of above |

EXAMPLE XI

The procedure of Example IX is followed except that the active ingredient is selected from, but not limited to, Table 2.

TABLE 2

| | |
|---|---|
| Antimuscarinic agents | hyoscyamine sulfate, atropine, methantheline bromide, emepronium bromide, anisotropine methyl bromide, and their derivatives |
| Anticholinergic agents | propantheline bromide, imipramine, mepenzolate bromide, isopropamide iodide, clidinium bromide, anisotropine methyl bromide, scopolamine hydrochloride, and their derivatives. |
| Antispasmodic agents | hexadiphane, magnesium gluconate, oktaverine, alibendon, butamiverine, hexahydroadiphene, 2-piperidinoethyl 3-methylflavone-8-carboxylate, 4-methylumbelliferone O,O-diethyl phosphorothiate |
| Calcium antagonist agents | terodiline and its derivatives |
| Potassium channel openers | pinacidil and N-[-2-Nitrooxy)ethyl]-3-pyridinecarboxamide |
| Musculotropic relaxants | dicyclomine hydrochloride, flavoxate hydrochloride, papaverine hydrochloride, oxybutynin chloride, and their derivatives |
| Antineoplastic agents | carmustine levamisole hydrochloride, flutamide, (w-methyl-N-[4-nitro-3-(trifluoromethyl)phenyl]), adriamycin, doxorubicin hydrochloride, idamycin, fluorouracil, cytoxan, mutamycin, mustargen and leucovorin calcium |
| Polysynaptic inhibitors | baclofen and its derivatives |
| β-adrenergic stimulators | terbutaline and its derivatives |

EXAMPLE XII

The procedure of Example IX is followed except that the container is selected from Table 3.

Table 3

Silicone
Stainless steel
Titanium
Plastics
Gold
Silastic
Platinum
Metal alloys

EXAMPLE XIII

Blend 100 g of doxorubicin, 100 g of hyoscymine and 500 g of oxybutynin with 10 kg of polylactide polymer. A fiber is made by extruding the blend through an orifice of 3 mm in diameter. It is then coated with a 10 micron thick coating of hydrophobic polyurethane and cut into 1 mm lengths. Approximately 10 discs are packaged under vacuum and gamma irradiated with 2.0 mRad. The device is ready to be inserted into the patient's prostate or bladder neck submucosally.

EXAMPLE XIV

Under aseptic conditions, fifty grams of diphenhydramine hydrochloride, USP grade, and 400 milligrams of USP grade atropine are blended into 1.0 kg of polylactide-glycolide (80:20) copolymer. A fiber is made by extruding through an orifice which is 1 mm by 1 mm. The fiber is coated with a 10 micron layer of gold using a vacuum sputtering method and then cut into 1.5 mm length. Approximately 10 of these rectangles are packaged under vacuum.

It should be understood, of course, that the foregoing relate only to preferred embodiments of the present invention and that numerous modifications or alterations may be made therein without departing from the spirit and scope of the invention as set forth in the appended claims.

I claim:

1. An implant device for the long term delivery of a therapeutic agent to a tissue or organ, comprising:
   a container for implantation within the tissue or organ; and
   a therapeutic agent immobilized in a biodegradable matrix wherein said matrix is biodegradable by enzymatic or acid/base hydrolysis and contained within the container such that the therapeutic agent is released at a rate of at least approximately 0.1 µg/day over a period of at least approximately one month, said device having a diameter of between approximately 20 microns and approximately 3 cm.

2. The implant device of claim 1, wherein the container is comprised of a material which is impermeable to macromolecules.

3. The implant device of claim 2, wherein the rate of release of the therapeutic agent is controlled by a portion of the container being permeable to the therapeutic agent.

4. The implant device of claim 2, wherein the rate of release of the therapeutic agent is further controlled by controlling the permeability of the permeable portion.

5. The implant device of claim 2, wherein the rate of release of the therapeutic agent is further controlled by controlling the dimensions of the permeable portion.

6. The implant device of claim 1, wherein the rate of release is controlled by controlling the rate of biodegradation of the biodegradable matrix.

7. The implant device of claim 1, wherein the therapeutic agent is selected from the group consisting of antimuscarinic agents, anticholinergic agents, antispasmodic agents, calcium antagonist agents, potassium channel openers, musculotropic relaxants, polysynaptic inhibitors, beta-adrenergic stimulators and antitumor agents.

8. The implant device of claim 1, wherein the therapeutic agent is selected from the group consisting of propantheline bromide, imipramine, hyoscyamine sulfate, oxybutynin chloride, carmustine, dicyclomine and terodiline.

9. The implant device of claim 1, wherein the biodegradable matrix is selected from the group consisting of polylactide, polyanhydrides, polyglycolide, polylactide co-glycolide polypeptides, poly(ortho)esters, hyaluronic acid, collagen, chondroitin sulfate, carboxylic acids, phospholipids, polysaccharides, polyamino acids, nucleic acids, phenylalanine, tyrosine, isoleucine, polynucleotides, polyethylene glycol, polyvinyl propylene, polyvinylpyrrolidone and beeswax.

10. The implant device of claim 1, wherein the container is a cylinder.

11. The implant device of claim 2, wherein the material which is impermeable to macromolecules is selected from the group consisting of stainless steel, gold, titanium, platinum, metal alloys, silicone, silastic and plastics.

12. The implant device of claim 11, wherein the plastic is selected from the group consisting of polyethylene, polypropylene, polycarbonate, polystyrene, polyethylene terephthalates, polyurethane and parylene.

13. A method of treating a tissue or organ comprising the step of implanting an implant device into the tissue or organ, the implant device comprising:

a container for implantation within the tissue or organ; and a therapeutic agent immobilized in a biodegradable matrix wherein said matrix is biodegradable by enzymatic or acid/base hydrolysis and contained within the container such that the therapeutic agent is released at a rate of at least approximately 0.1 µg/day over a period of at least approximately one month, said device having a diameter of between approximately 20 microns and approximately 3 cm.

14. The method of claim 13, wherein the container is comprised of a material which is impermeable to macromolecules.

15. The method of claim 13, wherein the rate of release of the therapeutic agent is controlled by a portion of the container being permeable to the therapeutic agent.

16. The method of claim 15, wherein the rate of release of the therapeutic agent is further controlled by controlling the permeability of the permeable portion.

17. The method of claim 15, wherein the rate of release of the therapeutic agent is controlled by controlling the dimensions of the permeable portion.

18. The method of claim 13, wherein the rate of release is controlled by controlling the rate of biodegradation of the biodegradable matrix.

19. The method of claim 13, wherein the therapeutic agent is selected from the group consisting of antimuscarinic agents, anticholinergic agents, antispasmodic agents, calcium antagonist agents, potassium channel openers, musculotropic relaxants, polysynaptic inhibitors, beta-adrenergic stimulators and antitumor agents.

20. The method of claim 19, wherein the therapeutic agent is propantheline bromide, imipramine, hyoscyamine sulfate, carmustine, oxybutynin chloride, dicyclomine and terodiline.

21. The method of claim 18, wherein the biodegradable matrix is selected from the group consisting of polylactide, polyanhydrides, polyglycolide, polylactide co-glycolide polypeptides, poly(ortho)esters, hyaluronic acid, collagen, chondroitin sulfate, carboxylic acids, phospholipids, polysaccharides, polyamino acids, nucleic acids, phenylalanine, tyrosine, isoleucine, polynucleotides, polyethylene glycol, polyvinyl propylene, polyvinylpyrrolidone and beeswax.

22. The method of claim 13, wherein the container is a cylinder.

23. The method of claim 14, wherein the material which is impermeable to macromolecules is selected from the group consisting of stainless steel, gold, titanium, platinum, metal alloys, silicone, silastic and plastics.

24. The implant device of claim 23, wherein the plastic is selected from the group consisting of polyethylene, polypropylene, polycarbonate, polystyrene, polyethylene terephthalates, polyurethane and parylene.

* * * * *